United States Patent [19]

Blarer et al.

[11] Patent Number: 5,071,871
[45] Date of Patent: Dec. 10, 1991

[54] PHARMACEUTICALLY USEFUL BENZO(BETA)PYRANES AND PYRANOPYRIDINES

[75] Inventors: Stefan Blarer, Basel; John Morley, Muttenz; Ian D. Chapman, Basel, all of Switzerland

[73] Assignee: Sandoz Ltd., Basel, Switzerland

[21] Appl. No.: 550,590

[22] Filed: Jul. 10, 1990

Related U.S. Application Data

[63] Continuation-in-part of Ser. No. 474,590, Feb. 1, 1990, abandoned, which is a continuation of Ser. No. 193,974, May 13, 1988, abandoned.

[30] Foreign Application Priority Data

May 16, 1987 [DE] Fed. Rep. of Germany ....... 3716523

[51] Int. Cl.$^5$ ..................... A61K 31/35; C07D 311/22
[52] U.S. Cl. ................................ 514/456; 514/210;
514/212; 514/218; 514/228.8; 514/258;
514/302; 514/337; 514/369; 514/376; 514/392;
514/422; 514/432; 514/444; 544/54; 544/55;
544/96; 544/278; 544/310; 544/317; 544/319;
544/328; 546/15; 546/116; 546/116; 546/269;
548/225; 548/226; 548/230; 548/234; 548/318;
548/336; 548/525; 549/9; 549/28; 549/60;
549/264; 549/271; 549/292; 549/293; 549/313;
549/320; 549/345; 549/346; 549/399; 549/400;
549/401; 549/404
[58] Field of Search ........................ 549/9, 28, 60, 264,
549/271, 292, 293, 313, 320, 346, 345, 399, 400,
401, 404; 546/15, 115, 116, 117, 269; 544/54,
55, 278, 96, 310, 317, 319, 328; 548/225, 226,
230, 234, 318, 336, 525; 514/210, 212, 218,
228.8, 258, 302, 337, 369, 376, 392, 422, 432,
444, 456; 540/488, 492, 524, 544, 553, 597, 599

[56] References Cited

U.S. PATENT DOCUMENTS 4,555,509 11/1985 Evans et al. .
4,758,677 7/1988 Evans et al. .

FOREIGN PATENT DOCUMENTS 0107423 5/1984 European Pat. Off. .

OTHER PUBLICATIONS

Chem. Abstract 69:113385, Egorova et al. (1968).
J. Chem. Inc. Perkin Trans (1), Bateman et al., 2903–2912 (1983).

Primary Examiner—Bernard Dentz
Attorney, Agent, or Firm—Gerald D. Sharkin; Robert S. Honor; Thomas O. McGovern

[57] ABSTRACT

New benz[b]pyranes and pyranopyridines of formula I,

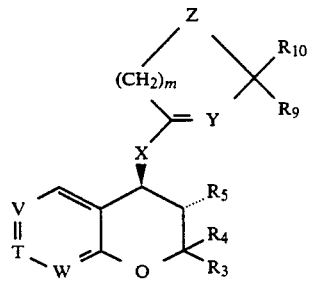

wherein the significances of substituents V, T, W, $R_3$ to $R_5$, $R_9$, $R_{10}$, m, X, Y and Z are given in claim 1 and their N-oxides and their salts and their use in the treatment of raised blood pressure in the treatment of vascular disorders and other disorders in which a reduction in tension of the smooth muscles is therapeutically useful, as well as in the treatment of hair loss and baldness. Further the compounds are useful in the treatment of asthma and obstructive disorders of the respiratory system as well as in the prophylactic treatment of obstructive or inflammatory airways disease, for example asthma, as well as novel pharmaceutical compositions comprising said K+ channel activators suitable for such use.

21 Claims, No Drawings

PHARMACEUTICALLY USEFUL BENZO(BETA)PYRANES AND PYRANOPYRIDINES

This application is a continuation-in-part of U.S. patent application Ser. No. 7/474,590, filed Feb. 1, 1990, now abandoned, which in turn is a continuation of U.S. patent application Ser. No. 7/193,974, filed May 13, 1988, now abandoned.

The invention relates to new benzo[b]pyranes and pyranopyridines, of formula

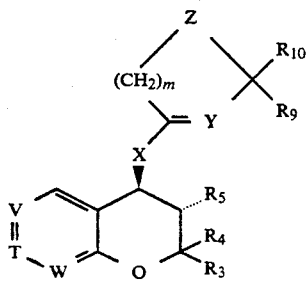

wherein either

A) V denotes $R_1$—C, T denotes $R_2$—C and W denotes H—C, wherein $R_1$ signifies hydrogen, halogen, ethynyl, hydroxy, cyano or the groups of formulae —$NR_6R_8$, —$CO_2R_6$ or —$CONR_6R_7$ and $R_2$ signifies hydrogen, halogen, ($C_{1-4}$)alkoxy, hydroxy or the group of formula —$NR_6R_8$— whereby $R_6$ and $R_7$ independently of one another respectively denote hydrogen or a ($C_{1-4}$)alkyl group and $R_8$ signifies hydrogen, a ($C_{1-4}$)alkyl group, a formyl, an acetyl or a trifluoroacetyl group—or one of $R_1$ and $R_2$ signifies nitro and the other of $R_1$ and $R_2$ is defined as above, or B) V denotes N or the corresponding N-Oxide, T denotes $R_2$—C wherein $R_2$ has the significance given above and W denotes HC, or C) V denotes $R_1'$—C, T denotes H—C and W denotes N, wherein $R_1'$ signifies hydrogen, a cyano or nitro group or D) V denotes N, T denotes H—C and W denotes N, $R_3$ and $R_4$ independently of one another, denote hydrogen or a ($C_{1-4}$) alkyl group or $R_3$ and $R_4$ together signify a group —$(CH_2)n$—, whereby n is 2, 3, 4 or 5, $R_5$ signifies hydrogen or $OR_8$, wherein $R_8$ is defined as above, $R_9$ and $R_{10}$ respectively denote hydrogen or methyl or together signify an oxo- or a thio-group, m is 1,2 or 3, X signifies O or $NR_{11}$, whereby $R_{11}$ signifies hydrogen, a ($C_{1-4}$) alkyl-, formyl-, acetyl- or hydroxymethyl group, Y=CH, C-halogen, N, C-formyl or C-hydroxymethyl and Z=$CH_2$, O, S, CH-halogen or $NR_6$, wherein $R_6$ is defined as above, as well as their N-Oxides, their pharmacologically acceptable acid addition salts and quaternary ammonium salts.

Of the compounds of formula I, preferred compounds possess formula Ia,

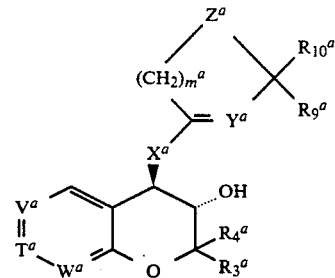

wherein either $A^a$) $V^a$ denotes $R_1{}^a$—C, $T^a$ denotes $R_2{}^a$—C and $W^a$ denotes H—C, wherein $R_1{}^a$ signifies hydrogen, cyano, halogen, —$NR_6R_8$ ethynyl or a group —$CO_2R_6$ or —$CONR_6R_7$ and $R_2{}^a$ signifies hydrogen, methoxy, hydroxy or a group of formula —$NR_6R_8$, wherein $R_6$, $R_7$ and $R_8$ have the significance given above, or one of $R_1{}^a$ and $R_2{}^b$ denotes nitro and the other of $R_1{}^a$ and $R_2{}^a$ is defined as above, or $B^a$) $V^a$ denotes N or the corresponding N-Oxide, $T^a$ denotes $R_2{}^a$—C wherein $R_2{}^a$ has the significance given above and $W^a$ denotes H—C, or $C^a$) $V^a$ denotes $R_1{}^{a'}$—C, $T^a$ denotes H—C and $W^a$ denotes N, wherein $R_1{}^{a'}$ signifies hydrogen, cyano or nitro or $D^a$) $V^a$ denotes N, $T^a$ denotes H—C and $W^a$ denotes N $R_3{}^a$ and $R_4{}^a$ respectively signify hydrogen or ($C_{1-4}$)alkyl or $R_3{}^a$ and $R_4{}^a$ together form a group of formula —$(CH_2)n^a$, wherein $n^a$ signifies 2,3 or 4

$R_9{}^a$ and $R_{10}{}^a$ respectively signify hydrogen or methyl or together signify an oxo group, $m^a=1$ or 2

$X^a$ denotes O or $NR_{11}$, wherein $R_{11}$ possesses the definition given above $Y^a$ denotes CH, C-halogen, C-hydroxymethyl, C-formyl or N and $Z^a$ denotes O, $NR_6$, wherein $R_6$ possesses the definition given above, $CH_2$, CH-halogen or S, as well as their N-Oxides, their pharmacologically acceptable acid addition salts and quaternary ammonium salts.

Of the compounds of formula I, especially preferred compounds posses formula Ib,

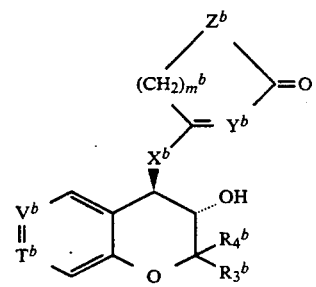

$A^b$) $V^b$ denotes $R_1{}^b$—C, $T^b$ denotes $R_2{}^b$—C, wherein $R_1{}^b$ signifies hydrogen, ethynyl, cyano or a group of formula —$NR_6R_8$, —$CO_2R_6$ or $CONR_6R_7$ and $R_2{}^b$ signifies hydrogen, hydroxy or a group of formula —$NR_6R_8$ wherein $R_6$, $R_7$ and $R_8$ have the significances given above, or one of $R_1{}^b$ and $R_2{}^b$ signifies nitro and the other of $R_1^b$ and $R_2^b$ is defined as above, or $B^b$) $V^b$ denotes N or the corresponding N-Oxide, $T^b$ denotes $R_2^b$—C, wherein $R_2^b$ has significance given above, $R_3^b$ and $R_4^b$ respectively signify hydrogen or $(C_{1-4})$alkyl, or $R_3^b$ and $R_4^b$ together signify a group of formula —$(CH_2)_{n^b}$—, wherein $n^b$ signifies 2,3 or 4, $m^b$ respectively denotes 1, or 2, and $X^b$ denotes O or $NR_{11}$, whereby $R_{11}$ possesses the definition given above, $Y^b$ denotes CH, C-halogen, C-hydroxymethyl, C-formyl or N and $Z^b$ denotes $CH_2$, CH-halogen, O, S or $NR_6$, wherein $R_6$ possesses the definition given above, as well as their N-Oxides, their pharmacologically acceptable acid addition salts and quaternary ammonium salts.

In formula I, halogen denotes fluorine, chlorine, bromine or iodine, preferably fluorine, bromine or iodine, especially fluorine or iodine, a $(C_{1-4})$alkoxy group denotes methoxy, ethoxy, n-propoxy or isopropoxy n-butoxy, i-butoxy, tert.-butoxy, especially methoxy, a $(C_{1-4})$alkyl group denotes methyl, ethyl, n-propyl, i-propyl, n-butyl, i-butyl, tert.-butyl especially methyl or ethyl.

The compounds of formula I, their N-Oxides their pharmacologically acceptable acid addition salts and quaternary ammonium salts are obtained by reaction of compounds of formula II,

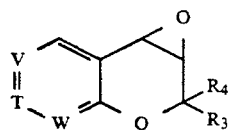

wherein V, T, W, $R_3$ and $R_4$ possess the definitions given above, with compounds of formula III,

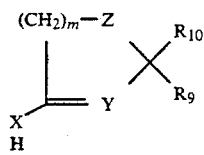

wherein $R_9$, $R_{10}$, X, Y, Z and m possess the definitions given above. The compounds thus obtained may optionally undergo further reactions, e.g. are subsequently converted into their N-Oxides and/or in their pharmacologically acceptable acid addition salts and quaternary ammonium salts.

The above process is effected in analogous manner, to the process described for example in European patent application no. 107.423. In this, the epoxide of formula II is reacted with the compounds of formula III, which are found in anionic form. This anionic form is formed in situ, under the influence of a strong base, for example sodium hydride.

To carry out the process according to the invention it is often convenient to catalyse the reaction, for example using catalytic or stochiometric quantities of copper(I)-bromide, magnesium bromide or titanium alkoxides, or to catalyse the epoxide opening with catalytic or stochiometric quantities of a lewis acid like $BF_3.OEt_2$. The reaction conveniently takes place in an inert solvent, for example in dimethylformamide, dimethyl sulphoxide, tetrahydrofuran, dimethylpropylene-urea or mixtures thereof, at low, medium or high temperatures, preferably at room temperature, i.e. ca. 20° to 25° C. It is often convenient for the compounds obtained according to the above process to undergo further reactions, for example addition of iodine to the cyclopentenyl ring, as is illustrated in examples 3 and 4.

The starting compounds used in the above processes are either known or may be produced from known starting compounds using the processes described in European patent application no.107.423 or in the example section of the present application.

The compounds of formula I produced according to the invention appear both in racemic form and in optically active form, and the processes described above starting with optically inactive educts, lead to a mixture of all these forms. The individual isomers may be separated from one another in known manner for example by chromatography, using a chiral phase. When optically active compounds of formula I are to be produced, optically active starting compounds are conveniently used, or synthesis is effected asymmetrically.

The free bases of the compounds of formula I may be converted into their salts. For example, acid addition salts can be produced in known manner, by a reaction with a suitable acid and vice versa. Acids which are suitable for salt formation are e.g. hydrochloric acid, hydrobromic acid, malonic acid, maleic acid, fumaric acid, benzene-sulphonic acid, toluene-sulphonic acid, methane-sulphonic acid, malic acid, tartaric acid, camphor-sulphonic acid, formic acid, oxalic acid, phosphoric acid, sulphuric acid, trifluoroacetic acid and trifluoro-methane-sulphonic acid. Quaternary ammonium salts of the compounds according to the invention may be produced in known manner, for example by a reaction with methyl iodide. N-Oxides of compounds of formula I can be prepared in a manner known per se at the end of the synthesis starting from compounds of formula I, e.g. by treatment with oxidizing agents like hydrogenperoxide, m-chloroperbenzoic acid or with Collin's Reagent ($CrO_3.Py_2$) or starting from oxidized intermediates. Of course, the acid addition salts, the quaternary ammonium salts and the N-Oxides of the compounds of formula I are all pharmacologically acceptable.

In the following examples, all temperatures are given in degree celsius and are uncorrected.

EXAMPLE 1 trans-3,4-dihydro-3-hydroxy-2,2-dimethyl-4-(3-oxo-1-cyclopent-1-enyloxy)-2H-1-benzopyran-6-carbonitrile 10.1 g of 1,3-cyclopentadione are dissolved in 1000 ml of tetrahydrofuran under a protective gas, and 2.7 g of sodium hydride (80%) are slowly added. After half an hour, 18.5 g copper(I)bromide.dimethylsulphide complex were added to this mixture. To this reaction solution are added in drops 12.1 g of 3,4-epoxy-3,4-dihydro-2,2-dimethyl-2H-1-benzopyran-6-carbonitrile (J. M. Evans et al., J. Med. Chem. 26, 1582 [1983]) in 100 ml of tetrahydrofuran. After 67 hours, the reaction is quenched with water, and the reaction solution is subsequently partitioned between dichloromethane and water. Drying of the organic phase over sodium sulphate, filtration and concentration on a rotary evaporator yields a yellowish mass, which is purified by flash-chromatography (dichlormethane, 1% methanol). Recrystallisation from dichloromethane/ethanol yields white crystals having a m.p. of 199°-201° C.

EXAMPLE 2 trans-3,4-dihydro-3-hydroxy-2,2-dimethyl-4-(3-oxo-1-cyclohex-1-enyloxy)-2H-1-benzopyran-carbonitrile 1.01 g of the epoxide of example 1 are reacted analogously to example 1 with 225 mg of sodium hydride 80%, 1.54 g of copper(I)bromide.dimethylsulphide complex and 841 mg of 1,3-cyclohexadione. The product obtained after the usual work up is crystallised from dichloromethane/diethylether to produce white crystals having a m.p. of 168°-70° C.

EXAMPLES 3 AND 4 trans-3,4-dihydro-3-hydroxy-2,2-dimethyl-4-(4-iodo-3-oxo-1-cyclopent-1-enyloxy)-2H-1-benzopyran-6-carbonitrile 2.0 g of the unsaturated compound of example 1 were etherified for 21 hours at room temperature in 60 ml of dichloromethane with 3.3 g of 3,4-dihydro-2H-pyran in the presence of 168 mg of pyridine-p-toluene sulphonate. Subsequent partitioning between water and diethylether, washing of the organic phase, drying over sodium sulphate and concentration yields a whitish mass, which is further processed directly.

Lithium-diisopropyl-amide is produced under argon in 15 ml of tetrahydrofuran from 1.01 g of diisopropylamine and 6.25 ml of butyllithium (1.6M in hexane). This solution is diluted at −78° C. with 3 ml of dimethylpropylene-urea, and is mixed with the above-obtained raw materials in 10 ml of tetrahydrofuran. After allowing to stand for one hour at −78° C., this solution is added to a solution, cooled to −78° C., of 1.7 g of iodine in 20 ml of tetrahydrofuran. After allowing the reaction to reach room temperature, the reaction is interrupted by adding water. The usual work up yields a red-brown resin, which is purified by flash-chromatography (dichlormethane, 0.2% methanol)

The intermediate products thus obtained were stirred for 5 days at 35° C. bath temperature in 10 ml of ethanol, 0.5 ml of water and 69 mg of pyridine-p-toluene sulphonate. Usual work up and chromatography (silica gel/dichlormethane, 0.2% methanol) of the crude products yield the two in position 5 iodinated diastereoisomers.

EXAMPLE 3 diastereoisomer A

A polar; m.p. 167°-168° C. (from dichlormethane/diethylether.

EXAMPLE 4 diastereoisomer B

Polar; m.p. 167°-169° C. (from ethyl acetate).

EXAMPLE 5 trans-3,4-dihydro-3-hydroxy-2,2-dimethyl-4-(3-oxo-1-cyclopent-1-enylamino)-2H-1-benzopyran-6-carbonitrile 2.41 g of the epoxide of example 1 were solved in 36 ml of dimethylsulfoxide under a protective gas, and 360 mg of sodium hydrid were added. To this stirred suspension was added 1.71 g of 3-amino-cyclopent-2-en-1-one (Chem. Ber. 103, 2403 [1970]) in portions. After 21 hours, the reaction solution was worked up in an aqueous manner and extracted with ethyl acetate. The usual further processing and recrystallisation of the product obtained from ethyl acetate yielded white crystals having a m.p. of 174°-176° C.

EXAMPLE 6

(+)-(3R,4S)-trans-3,4-dihydro-3-hydroxy-2,2-dimethyl-4-(3-oxo-1-cyclopent-1-enyloxy)-2H-1-benzopyran-6-carbonitrile 33,8 g of trans-3-bromo-2,2-dimethyl-4-hydroxy-2H-1-benzopyran-6-carbonitrile (J. M. Evans et al., J. Med. Chem. 26, 1582 [1983]) are dissolved in 300 ml of pyridine under argon and to this solution a solution of 28 g of (−) camphanic acid in 120 ml of methylenechloride is added slowly. After 2 hours the reaction solution is poured on 2N hydrochloric acid and extracted with methylenechloride. After washing of the organic phase with 0,5N hydrochloric acid, aqueous saturated sodium-bicarbonate solution and water and subsequent drying over sodiumsulphate and concentration a mixture of diastereoisomeres is obtained. After chromatography on silica gel/methylenechloride a diastereoisomer A [m.p. 193°-194° C. from methylenechloride/methanol; $[\alpha]_D^{20}=-41,3°$ (c=1, $CH_2Cl_2$); NMR pure diastereoisomer: ds 99%] and a diastereoisomer B [m.p 154°-55° C. from methylenechloride/methanol; $[\alpha]_D^{20}=+38,0°$ (c=1, $CH_2Cl_2$); ds>99%] and a mixture of A/B are obtained.

18,5 g of the apolar ester A is saponified with 88 ml of 1N aqueous sodiumhydroxide in 100 ml of dioxane during 90 minutes. After extraction of the reaction mixture with ether, washing of the organic phase with water and drying with sodium sulphate and concentration (+)-3,4-dihydro-3,4-epoxy-2,2-dimethyl-2H-1-benzopyran-6-carbonitrile is obtained, m.p. 144°–45° C. after crystallisation from ether/hexane; $[\alpha]_D^{20}=+86,6°$ (c=1,2, $CH_2Cl_2$). By acidification of the aqueous phase with 2N hydrochloric acid and subsequent extraction with ether (−)camphanic acid can be recovered.

706 mg of 1,3-cyclopentandione are dissolved in 100 ml of tetrahydrofuran under a protective gas and 216 mg of sodium hydride (80%) are added. After 45 minutes of stirring 1,21 g of the above (+)epoxide dissolved in 10 ml of tetrahydrofuran and 0,8 ml of borontrifluoride-ethyletherat are added to the reaction solution. After 3 hours the reaction solution is poured on a diluted aqueous sodium-bicarbonate solution and extrated with dichloromethane. Usual work up yields white crystalls of the title compound having a m.p. of 154°-50° C. (from dichloromethane/ether) and $[\alpha]_D^{20}=+129,9°$ (c=1,0 ethanol).

EXAMPLE 7

(−)-(3S,4R)-3,4-dihydro-3-hydroxy-2,2-dimethyl-4-(3-oxo-1-cyclopent-1-enyloxy)-2H-1-benzopyran-6-carbonitrile (−)-3,4-dihydro-2,2-dimethyl-3,4-epoxy-2H-1-benzopyran-6-carbonitrile obtained in example 6 from the diastereoisomeric ester B is reacted analogously to example 6 with equivalent amounts of 3-cyclopentadione. The obtained title compound melts at 154°-156° C. (from dichlormethane/ether); $[\alpha]_D^{20}=-129.1°$ (c=1,0 ethanol).

EXAMPLE 8 trans-3,4-dihydro-3-hydroxy-2,2-dimethyl-4-[2-oxofuran-4(5H)-ylamino]-2H-benzopyran-6-carbonitrile 34,5 mg of the epoxide of example 1 and 17 mg of 4-Amino-2-(5H)-furanone (CAS 92089-08-2) are reacted analogously to example 5 with sodium hydride in dimethylsulfoxide. The usual working up yields yellowish crystals of the title compound having a m.p. of 182° C. (from ethanol/dichloromethane, decomposition).

EXAMPLE 9 trans-3,4-dihydro-3-hydroxy-2,2-dimethyl-4-[2-oxofuran-4(5H)-yloxy]-2H-1-benzopyran-6-carbonitrile 601 mg of tetronic acid and 1.01 g of the epoxide of example 1 are reacted analogously to example 6 with 180 mg of sodium hydride (80%) and 747 mg of borontrifluoride-diethyletherate in tetrahydrofurane. Usual work up yields white crystals of the title compound. m.p. 111°-114° C. (dichloromethane/ether)

EXAMPLE 10 trans-3,4-dihydro-3-hydroxy-2,2-dimethyl-4-[N-methyl-N-(3-oxo-cyclopent-1-enyl)amino]-2H-1-benzopyran-6-carbonitrile 1,12 g 3-methoxy-cyclopent-2-en-1-on are reacted with 15 ml of methylamine (33% solution in ethanol) during 23 hours at 100° C. in an autoclave. Flash-chromatography (silica gel/dichloromethane, methanol 5%) on the concentrated raw material yields N-methyl-3-amino-cyclopent-2-en-1-on having a m.p. of 130°-31° C.

4.02 g of the epoxide of example 1 are reacted analogously to example 5 with 2.44 g N-methyl-3-amino-cyclopent-2-en-1-on and 660 mg of sodium hydride (80%) in dimethylsulfoxide. Usual working up yields crystals of the title compound having a m.p. of 271°-74° C.

EXAMPLE 11 trans-3,4-dihydro-3-hydroxy-2,2-dimethyl-4-[N-methyl-N-(2-oxyfuran-4(5H)-yl)amino]-2H-1-benzopyran-6-carbonitrile To a solution of 39 g acetoacetic acid ethylester in 180 ml of dichloromethane, 48 mg of bromine in 15 ml of dichloromethane are added dropwise at 0° C. under a protective gas. Hydrobromic acid is formed. After 25 minutes at 17° C. an oxigen stream is blown through the reaction mixture for one hour. After 90 mg of potassiumacetate have been added in one portion, 300 ml of glacial acetic are added dropwise during 10 minutes. The internal temperature is kept below 40° C. Then the reaction temperature is raised slowly to 80° C. whereby dichloromethane distills off. After further 5 hours at 80° C. the solution is concentrated on a rotary evaporation and the residue, after it has been extracted twice with toluene, is dissolved in 300 ml of dichloromethane. The solution is allowed to stand at 4° C. during the night. Destillation at 78°-85° C./0.2 bar yields a slightly yellowish 4-acetyloxy-acetylacetic acid ethylester.

In an extraction apparatus (soxhlet-apparatus) filled with molecular sieves 3A a solution of 1,88 g of the above ester in 20 ml ethanol, a catalytic amount of p-toluenesulphonic acid and 1,87 ml of a methylaminosolution (ethanol 33%) are heated to reflux during one hour. The concentrated intermediate is taken up in 25 ml of methanol, then mixed with 400 mg of dried potassium carbonate and heated to reflux during one hour. Addition of 500 mg of ammoniumchloride yields after concentration an orange mass that is washed twice with ethanol and purified further by flash-chromatography (silica gel, dichloromethane/methanol 2%). Recristallisation of the eluate from dichloromethane/ethanol yields N-methyl-4-amino-2(5H)-furanon having a m.p. of 177°-79° C. 1.01 g of the epoxide of example 1 in 15 ml of dimethylsulfoxide are reacted analogously to example 5 with 150 mg of sodium hydride and 566 mg of N-methyl-tetronic acid amide. Usual working up yields the title compound having a m.p. of 232°-34° C.

EXAMPLE 12 trans-3,4-dihydro-3-hydroxy-2,2-dimethyl-4-[N-methyl-N-(N-methyl-2-oxo-pyrrol-4(5H)-yl)amino]-2H-1-benzopyran-6-carbonitrile 3,14 g of 4-bromo-acetylacetic acid ethylester formed as intermediate in example 11, in 15 ml ethanol, 7,5 ml of a methylaminesolution (ethanol 33%) and a catalytical amount of p-toluenesulphonic acid are heated together to reflux for two hours in an extraction apparatus (soxhlet apparatus) filled with molecular sieve. Purification of the concentrated residue by flash-chromatography (silica gel/dichloromethane, methanol 1%) yields 3,4-bis-(N-methyl-amino)-crotonic acid.

850 mg of the above intermediate product in 40 ml of methanol are cyclised analogously to example 11 with 600 mg potassium carbonate. Work up in analogous manner yields after sublimation (115° C./0,2 bar) 4-(N-methyl-amino)-N-methyl-2(5H)-pyrrolon having a melting point of 132°-34° C.

402 mg of the epoxide of example 1 in 4 ml of dimethylsulfoxide are reacted analogously to example 5 with 60 mg of sodium hydride and 25.2 mg of the amide obtained above. Usual work up yields the title compound having a m.p. of 266°-69° C.

EXAMPLE 13 trans-3,4-dihydro-3-hydroxy-2,2-dimethyl-[2-oxothiophen-4(5H)-yloxy]-2H-1-benzopyran-6-carbonitrile 1,21 g of the epoxide of example 1 in 80 ml of tetrahydrofuran are reacted analogously to example 1 with 836 mg of thiotetronic acid, 216 mg sodium hydride (80%) and 896 mg borontrifluoride-diethyletherat. Usual working up yields white crystals of the title compound having a m.p. of 173°-74° C. (from dichloromethane/ether)

EXAMPLE 14 trans-4-[N-formyl-[N-(3-oxo-cyclopent-1-enyl)amino]-3,4-dihydro-3-hydroxy-2,2-dimethyl-2H-1-benzopyran-6-carbonitrile 1,49 of the title compound of example 5 are dissolved in 25 ml of tetrahydrofuran under a protective gas and reacted with 11 g of formyl-acetic acid anhydride (Org. Synth. 50, 1 (1970)). After stirring for seven hours the reddish suspension is concentrated and extracted twice with methanol. Usual work up yields white crystals of the title compound (from dichloromethane/ether). Boiling point: decomposition from 182° C. on.

EXAMPLE 15 trans-3,4-dihydro-3-hydroxy-4-[N-(2-hydroxymethyl-3-oxo-cyclopent-1-enyl)amino]-2,2-dimethyl-2H-1-benzopyran-6-carbonitrile 2,98 of the title compound of example 5 are dissolved in 150 ml of acetone and a drop of a phenolphtalein-solution and the solution is mixed with 2,5 ml of a 37% formaldehyde solution three times every hour. The pH-value of the solution is kept between 8 and 9 by controlled addition of 0,1 aq. sodium hydroxide-solution. After stirring during 5 hours the reaction solution is diluted with water and the organic components are extracted with dichloromethane. Usual work up yields white crystalls of the title compound having a m.p. of 218°–220° C. (from dichloromethane/ethanol).

EXAMPLE 16 trans-3,4-dihydro-4-(2-formyl-3-oxo-cyclopent-1-enyl)amino-3-hydroxy-2,2-dimethyl-2H-1-benzopyran-6-carbonitrile 1,31 g of the title compound of example 15 are oxidised with 2,04 g of Collin's reagent in 240 ml of dichloromethane during 10 minutes. Work up by extraction in dichloromethane/water and subsequent flash-chromatography (silica gel, dichloromethan, methanol 3%) yields after recristallisation from dichloromethane/ethanol the title compound having a m.p. of 255°–58° C.

EXAMPLE 17 trans-4-[N-(2-fluoro-3-oxo-cyclopent-1-enyl)amino]-3,4-dihydro-3-hydroxy-2,2-dimethyl-2H-1-benzopyran-6-carbonitrile 1,05 g of the title compound of example 5 are dissolved in 35 ml of dichloromethane and 35 ml of dioxane and the obtained solution is mixed with 700 mg of xenondifluoride. After stirring for 5 hours the nearly clear solution is poured on water and the organic components are extracted with dichloromethane. Working up by flash-chromatography (silica gel/dichloromethan, methanol 2%) yields after recristallisation from ethanol white crystals of the title compound having a m.p. of 250°–52° C.

EXAMPLE 18 trans-4-[N-(2-chloro-3-oxo-cyclopent-1-enyl)amino]-3,4-dihydro-3-hydroxy-2,2-dimethyl-2H-1-benzopyran-6-carbonitrile A solution of 150 mg of the title compound of example 5 in 5 ml of dichloromethan and 5 ml of dioxan is mixed with 77 mg of N-chloro-succinimide. After 50 minutes at room temperature the solution is poured on water and the organic components are extracted with dichloromethane/ethanol. Recristallisation of the raw product obtained after concentration yields white crystalls of the title compound having a m.p. of 288°–89° C.

EXAMPLE 19 trans-4-[N-(2-bromo-3-oxo-cyclopent-1-enyl)amino]-3,4-dihydro-3-hydroxy-2,2-dimethyl-2H-1-benzopyran-6-carbonitrile The title compound is prepared analogously to example 18 by replacing N-chloro-succinimide by equivalent amounts of N-bromosuccinimide. m.p. of the title compound is 231°–33° C. (from methanol/dichloromethane).

EXAMPLE 20

3-amino-[N-(trans-3,4-dihydro-2,2-dimethyl-3-hydroxy-6-nitro-2H(1)-benzopyran-4-yl)]-cyclopent-2-en-1-on 3,4-dihydro-3,4-epoxy-2,2-dimethyl-6-nitro-2H-1-benzopyran [J. Med. Chem. 26, 1582 (1983)] is reacted analogously to example 5 with equivalent amounts of 3-amino-cyclopent-2-en-3-on and sodium hydride in dimethylsulfoxide to give the title compound having a m.p. of 244°–45° C. (from dichloromethane).

EXAMPLE 21 trans-3,4-dihydro-3-hydroxy-2,2-dimethyl-4-[N-methyl-N-(2-oxo-furan-4(5H)-yl)-amino]-2H-1-benzopyran-6-carbonic acid-methylester 3,4-dihydro-3,4-epoxy-2,2-dimethyl-2H-1-benzopyran-6-carbonic acid methylester is reacted analogously to example 5 with equivalent amounts of N-methyl-4-amino-2-oxo-5H-furan (example 11) and sodium hydride to give the title compound having a m.p. of 240°–41° C. (from methanol).

EXAMPLE 22 trans-3,4-dihydro-3-hydroxy-2,2-dimethyl-4-[N-methyl-N-(2-oxo-furan-4(5H)-yl)-amino]-2H-1-benzopyran-6-carbonic acid-dimethylamide A solution of 1,74 g of the title compound of example 21 in 50 ml N,N-dimethylamine solution (33% in ethanol) is kept for 10 days in an autoclave at 100° C. Usual work up yields white crystals of the title compound having a m.p. of 229°–31° C. (from acetic acid ethylester)

EXAMPLE 23 trans-2,2-diethyl-3,4-dihydro-3-hydroxy-4-(3-oxo-cyclopent-1-enyloxy)-2H-1-benzopyran-6-carbonitrile A solution of 16,1 g of 3-acetyl-4-hydroxybenzonitrile in 200 ml of toluene, 21 ml of diethylketone and 10 ml of pyrrolidin is refluxed for 3½ hours in a Dean-Stark apparatus. The reaction solution cooled to room temperature is made alkaline with a 2N aq. sodium hydroxide solution and extracted with dichloroethane. The combined organic phases are washed with sodium hydroxidesolution and water, dried over sodiumsulfate and concentrated. The obtained residue is chromatographed on silica gel/dichloromethane. Recristallisation of the eluate from ether/hexane yields 2,2-diethyl-3,4-dihydro-4-oxo-2H-1-benzopyran-6-carbonitrile having a m.p. of 71°–72° C.

13,7 g of this 4-chromanone are dissolved in 420 ml ethanol and the obtained solution is mixed with 1,14 g of sodiumborhydride. After 5 hours at room temperature the reaction solution is partitioned between water and dichloromethane, the organic phases are dried over sodiumsulphate and concentrated. 15 g of the obtained residue are taken up in 600 ml of toluene and are refluxed for 5 hours together with 570 mg of p-toluenesulphonic acid in a Dean Stark apparatus. Washing of the reaction solution with 2N aq. sodium hydroxide solution and water yields after drying over sodiumsulphate and concentration a residue that is purified by flash-chromatography (silica gel/dichloromethane, hexane 1:2). Concentration of the eluate gives 2,2-diethyl-1-benzopyran-6-carbonitrile as colorless oil.

12 g of the above chromene are dissolved in 400 ml of abs. dichloromethane, the obtained solution is mixed with anhydrous sodium bicarbonate and oxidized during 3 days with 31 mg of m-chloroperbenzoic acid. The slightly yellow suspension is partitioned between an aq. ammoniumhydroxide solution (5%) and dichlormethane, the organic phases are washed with water and dried over sodiumsulphate. The oil, obtained after concentration, is purified by flash-chromatography (silica gel/dichloromethane, hexane 2:3). Besides of educt, 2,2-diethyl-3,4-epoxy-3,4-dihydro-2H-1-benzopyran-6-carbonitrile is obtained as colorless oil.

1,61 g of the above epoxide are dissolved in 120 ml of tetrahydrofuran and reacted analogously to example 6 with 1,03 g of 1,3-cyclopentadione, 315 mg of sodium hydride (80%) and 1,05 g of borontrifluoride-diethyletherate. Usual working up yields after cristallisation from dichloromethane/methanol white crystalls of the title compound having a m.p. of 166°–70° C.

EXAMPLE 24 trans-3,4-dihydro-3-hydroxy-4-(3-oxo-cyclopent-1-enyloxy)-spiro[2H-1-benzopyran-2,1'-cyclohexan]-6-carbonitrile Starting from equivalent amounts of 3-acetyl-4-hydroxybenzonitrile and cyclohexanone in the presence of pyrrolidine there are obtained analogously to example 23 the following compounds:
3,4-Dihydro-4-oxo-spiro[2H-1-benzopyran-2,1'-cyclohexan]-6-carbonitrile: m.p. 92°–93° C. (from Ether/Hexane).
3,4-Dihydro-4-hydroxy-spiro[2H-1-benzopyran-2,1'-cyclohexane]-6-carbonitrile: Resin.
Spiro[2H-1-benzopyran-2,1'-cyclohexan]-6-carbonitrile: m.p. 93°–94° C. (from Dichlormethan/Hexan).
3,4-Dihydro-3,4-epoxy-spiro[2H-1-benzopyran-2,1'-cyclohexan]-6-carbonitrile
The title compound has a m.p. of 222°–25° C. (from Dichlormethan/Methanol)

EXAMPLE 25 trans-3,4-dihydro-2,2-dimethyl-4-(3-oxo-cyclopent-1-enyloxy)-2H-1-benzopyran-6-carbonitrile Starting from equivalent amounts of 3-acetyl-4-hydroxybenzonitrile and dimethylketone in the presence of pyrrolidine there are obtained analogously to example 23 the following compounds:
3,4-Dihydro-2,2-dimethyl-4-oxo-2H-1-benzopyran-6-carbonitrile: m.p. 124°–26° C. (from Ether/Hexan).
3,4-Dihydro-4-hydroxy-2,2-dimethyl-2H-1-benzopyrano-6-carbonitrile: colorless resin.

609 mg of this alcohol is deprotonated in 10 ml of tetrahydrofuran under protective gas with sodium hydride (80%). The reaction mixture is slowly mixed at 0° C. with a solution of 350 mg of 3-chloro-cyclopent-2-en-1-on in 2 ml of tetrahydrofuran. After 90 minutes the reaction mixture is worked up by partitioning between water and acetic acid ethylester. Purification of the concentrated and dried raw product by flash-chromatography (silica gel/acetic acid ethyl ester, hexane 1:1) yields a resin that is recrystallised from ethanol/ether. The title compound melts at 129°–30° C.

EXAMPLE 26

3-amino-N-(trans-3,4-dihydro-3-hydroxy-2,2-dimethyl-2H-pyrano[3,2-c]pyridin-4-yl)cyclopent-2-en-1-on To a solution of 258 mg of trans-3-bromo-3,4-dihydro-2,2-dimethyl-2H-pyrano[3,2-c]pyridin-4-ol (EP 205292 A) in ether 258 mg of powdered potassiumhydroxide are added and the obtained mixture is stirred during 2 hours at room temperature. The reaction mixture is taken up in ether and filtrated over talcum. The filtrate is concentrated to dryness and the obtained oil is reacted analogously to example 1 in 3 ml of dimethylsulfoxide with 97 mg of 3-amino-cyclopent-2-en-1-on and 30 mg of sodium hydride 80%. Working up by partitioning between acetic acid ethylester and 1N aq. sodium hydroxide solution yields after concentration and drying over magnesium white crystals of the title compound having a melting point of more than 300° C. (from ethanol/dichloromethane).

EXAMPLE 27

3-amino-N-(trans-3,4-dihydro-3-hydroxy-2,2-dimethyl-2H-pyrano[3,2-c]pyridin-4-yl)cyclopent-2-en-1-on-N-oxide To a white suspension of 7,9 mg of m-chloroperbenzoic acid and 4,4 g of dry sodiumbicarbonate in 90 ml of abs. chloroform a solution of 6,7 g of trans-3-bromo-3,4-dihydro-4-hydroxy-2,2-dimethyl-2H-pyrano[3,2-c]pyridin in 70 ml of chloroform is dropwise added under argon. After 2 hours the suspension is concentrated to dryness, the residue taken up in dichloromethane/methanol and filtrated to a clean filtrate. Concentration of the filtrate and purification by chromatography (silica gel, dichloromethan/methanol) of the residue yields solid trans-3-bromo-3,4-dihydro-4-hydroxy-2,2-dimethyl-6-oxido-2H-pyrano-[3,2-c]pyridine.

750 mg of this bromohydrins are dissolved in 7,5 ml of dioxan and 3,7 ml of water are cyclised with 4 ml 1N aq. sodiumhydroxide solution to the epoxide. Usual work up yields a white mass which is analogously to example 5 reacted with equivalent amounts of 3-amino-cyclopent-Z-en-1-on and sodium hydride in dimethylsulfoxide to give the title compound having a decomposition point from 247° C. on.

EXAMPLE 28 trans-N-acetyl-2,2-diethyl-7-amino-3,4-dihydro-3-hydroxy-4-(3-oxo-cyclopent-1-enyloxy)-2H-1-benzopyran-6-carbonitrile 4-amino-5-cyano-2-hydroxy-acetophenone (J. Chem. Soc. 1979, 677) is reacted analogously to example 23 to give 7-amino-2,2-dimethyl-2H-benzopyran-6-carbonitrile. This carbonitrile is acetylated and epoxidated as described in J. Chem. Med. 1984, 1130. Reaction of this epoxide analogously to example 6 with equivalent amounts of cyclopenta-1,3-dion and usual work up yields the title compound having a m.p. of 191° to 193° C.

EXAMPLE 29

3-(trans-N-acetyl-6-amino-3,4-dihydro-3-hydroxy-7-nitro-2,2-dimethyl-2H-1-benzopyran-4-oxy)-cyclopent-2-en-1-on N-acetyl-6-amino-3,4-epoxy-3,4-dihydro-2,2-dimethyl-7-nitro-2H-benzopyran (J. Med. Chem. 1984, 1130) is reacted analogously to example 6 with equivalent amounts of cyclopentadione. Usual working up yields white cristals of the title compound having a m.p. of 197°–199° C.

The compounds of formula I, their N-oxides and their salts are notable for their favourable, therapeutic activity. Measurements of tension in and of $^{86}Rb+$ efflux from various smooth muscle preparations according to the method of Quast (Brit. J. Pharmac. 91, (1987), 569–578) show that these substances relax smooth muscles and that they increase the potassium permeability of the smooth muscle cell membrane. The compounds of formula I, their N-oxides and their salts thus have extremely advantageous, blood pressure reducing activity and can therefore be used in the treatment of raised blood pressure.

The compounds of formula I, their N-oxides and their salts reduce blood pressure of anaesthetised, normotensive rats and rabbits, depending on concentration, following introduodenal administration of 0.03 to 100 mg/kg. The blood pressure reduction is maintained for ca. 6 hours.

The compound of example 7 having the formula

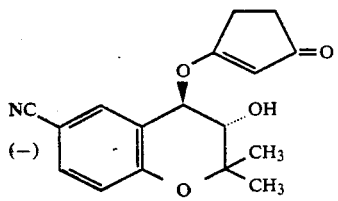

referred to hereinafter as PCO 400 is preferred according to the invention. This compound is active in the above test at dosages of from 0.03 mg/kg to 10 mg/kg.

The above experiment is carried out such that male OFA rats of 300 to 400 g weight are firstly anaesthetised with 150 mg/kg INACTIN. The femoral artery is cannulated to measure blood pressure and heart rate. After waiting for one hour, the test substance is administered introduodenally or intravenously. Following this, blood pressure and heart rate are measured for 6 hours.

The results obtained in the above test show that the compounds of formula I, their N-oxides and their salts may be used as antihypertensive agents.

Because of the vasodilating activity discovered, these compounds are similarly useful in the treatment of chronic cardiac insufficiency.

The quantity to be administered daily to large mammals is 1 to 100 mg, preferably 2 to 50 mg, especially 3 to 25 mg per day, whereby administration may take place 1 to 2 times daily in doses of 0.5 to 100 mg, preferably 1 to 50 mg, especially 1,5 to 25 mg.

Administration forms which are suitable for oral administration should contain from 1 to 100 mg of the compounds of formula I their N-Oxides or their salts, together with solid and liquid pharmaceutical carriers or diluents, and they are administered 1 to 2 times daily.

Additional experiments indicate that the compounds of formula I, their N-oxides and their salts are also therapeutically useful for vascular disorders, resp. disturbed blood supply e.g. to the heart, to skeletal muscle (e.g. in Claudication Intermittens and Morbus Reynaud) and to the brain.

The quantity to be orally administered daily to large mammals in this indication is 2 to 50 mg, especially 3 to 25 mg and administration can occur in the same way as for treatment of high blood pressure. Furthermore the compounds according to formula I, their N-Oxides and their salt have a relaxing effect on smooth muscles of the gastro-intestinal tract the uterus and the urinary tract. The outcome of this are therapeutical applications e.g. in disorders of the gastrointestinal tract, such as duodenal and peptic ulcers, irritable colon and diverticulitis, when there is danger of miscarriage following premature labour and incontinence.

The compounds according to formula I and their N-oxides may be administered in free base form or in the form of pharmaceutically acceptable salts, for example suitable acid addition salts and quaternary ammonium salts. Such salts have the same order of activity as the free base forms. The present invention accordingly also relates to a pharmaceutical composition which contains 10% by weight or more of a compound of formula I, an N-oxide and/or and acid addition salt and/or a quaternary ammonium salt thereof, together with a pharmaceutical carrier or diluent. Such compositions may be prepared in known manner and are administered for example in the form of solutions or tablets.

In addition the compounds of the formula I, their N-oxides and their salts have the potential to stimulate hair growth as described by Cook, Trends in Pharmacol. Sci 9,21 (1988). They may be useful where failure of growth including hair loss, is due to ageing, e.g. male alopecia, or where it is disease-related, i e consequential to disease, e.g. infection, or where the disease has an aetiology comprising a disturbance of the immune system.

The said compounds can accordingly be employed either for purely cosmetic purposes, e.g. for counteracting hair loss or baldness, e.g. pattern baldness, consequential to the natural process of ageing (and whether or not the onset of baldness is premature), as well as for primarily cosmetic purposes, e.g. for counteracting disease-related hair-loss or baldness.

It will be appeciated that where compounds of formula I, their N-oxides and salts are applied orally in accordance with the method of the invention, the compound must necessarily be pharmaceutically acceptable, i.e. physiologically tolerable, at the dosages to be administered. Where application is topical, the compound must be acceptable for topical administration. Where compounds to be applied orally contain physiologically metabolisable groupings, then these metabolites must also be pharmaceutically acceptable.

Where oral administration is considered, salt forms used are the above described pharmaceutically acceptable salts. Where topical administration is considered, salt forms are those described above and are acceptable for topical application.

Although the compounds of formula I, their N-oxides and salts for use in the method of the invention may be applied either orally or topically, since it will be more commonly desired to stimulate hair growth at a particular site on the body, for example the scalp, and targeting is more readily effected via topical application, topical application is generally preferred.

In accordance with the present invention it has further been found that compounds of formula I, their N-oxides and their salts are also capable of suppressing, diminishing or abrogating basal pathology of obstructive or inflammatory airways diseases, e.g. of suppressing, diminishing or abrogating airways hyperreactivity or pulmonary eosinophil accumulation causal to or inherent in the aetiology of such diseases. Compounds of formula I, their N-oxides and their salts are thus now found to be useful not only for the treatment of asthma and obstructive disorders of the respiratory system as can be deduced from the spasmolytic effect on airway smooth muscles as demonstrated by the inhibition of spontaneous tone in tracheal rings from the guinea pigs according to the method of Person and Ekman (Agents and Actions 6, 389 (1976))—PCO 400 showed activity from $10^{-7}$ to $3.10^{-4}$ mol/l but also for the prophylaxis of obstructive or inflammatory airways diseases, i.e. they are also capable, following advance administration, of preventing or reducing the occurrence or frequency of disease symptoms, e.g. acute bronchoconstriction. This is in marked contrast to drugs employed symptomatically, i.e. to alleviate disease symptoms as and when they occur and which may have no influence on essential disease pathology.

With respect to their prophylactic utility in the treatment of inflammatory airways diseases it has, in accordance with the invention, in particular been found that compounds of formula I, their N-oxides and their salts:
a) inhibit acute response in hypersensitive subjects following allergen or other challenge eliciting hypersensitivity reaction (e.g. following induction of hyperreactivity and airways obstruction via PAF challenge);
b) suppress development of airways hyperreactivity subsequent to challenge as under a);
c) reverse recently established exacerbation of airways hyperreactivity; and
d) diminish basal, or on-going, airways hyperreactivity, as evidenced in test methods as described hereinafter.
[For further discussion of the relevance of a), b) and c) above and their relationship to prophylactic use in treating inflammatory airways diseases, see e.g.: Altounyan, Clin. Allergy (supp) 10 481 (1980); Morley et al; Lancet ii, 1142 (1984); Mazoni et al; J Physiol 365 107P (1985); Traietti et al,; Respiration 46 62 (1984); Taytard et al; Am Rev Respiratory Disease 134 983 (1986); Szezeklik et al; Thrombosis and Haematosis 56 283 (1986); Basran et al; Clin Allergy 14 75 (1984); Karlsson et al; Brit J Clin Pharmacol 27 371 (1985); and Mazzoni et al; Brit J Pharmacol 86 571P (1985)].

Compounds of formula I, their N-oxides and their salts may thus be used for the prophylactic treatment of obstructive or inflammatory airways diseases, e.g. asthma. In particular, by continued administration they may be used to provide advance protection against bronchoconstrictor attack consequential to obstructive or inflammatory airways diseases, in particular asthma, or for the control, restriction or reversal of basal pathology of such diseases, e.g. for the control, restriction or reversal of basal causes of asthma and asthma attack, e.g. airways hyperreactivity.

In accordance with the foregoing the present invention provides in a series of embodiments:
A. A method for the prophylactic treatment of obstructive or inflammatory airways diseases in a subject in need thereof, which method comprises administering to said subject an effective amount of compounds of formula I, their N-oxides and their salts.
B. A method for the treatment (e.g. control, restriction or reversal) of basal pathology of inflammatory or obstructive airways diseases (e.g. of airways-hyperreactivity) in a subject in need thereof, which method comprises administering to said subject an effective amount of compounds of formula I, their N-oxides and their salts.
C. A method for the prophylactic treatment of obstructive or inflammatory airways diseases (e.g. for advance protective treatment against acute airways obstruction, for example bronchospasm, e.g. as occurring in the symptomatology of diseases, disorders or conditions as herein set forth) in a subject in need thereof, which method comprises administering to said subject a prophylactically effective amount of compounds of formula I, their N-oxides and their salts.

The method of the present invention as defined under A to C above is, in particular, applicable to the treatment of asthma of whatever type or genesis. It is applicable to both intrinsic and, especially, extrinsic asthma. It is especially applicable to the treatment of allergic asthma, whether atopic, (i.e. IgE-mediated) or non-atopic, as well as e.g. bronchitic asthma, exercise induced asthma, occupational asthma, asthma induced following bacterial infection and other non-allergic asthmas. Treatment of asthma is also to be understood as embracing treatment of subjects, e g. of less than 4 or 5 years of age, exhibiting wheezing symptoms, in particular at night, and diagnosed or diagnosable as "wheezy infants", an established patient category of major medical concern and now more correctly identified as incipient or early-phase asthmatics. (For convenience of definition this particular asthmatic condition is referred to hereinafter as "wheezy-infant syndrome".)

The method of the present invention as defined under A to C above is also applicable to the treatment of pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and, in particular, byssinosis.

Prophylactic efficacy of compounds of formula I, their N-oxides and their salts when employed in accordance with the methods of the invention, e.g. for the treatment of specific diseases or conditions as set forth above, will be evidenced by reduced frequency or severity of symptomatic attack, e.g. acute asthmatic or bronchoconstrictor attack in the subject treated. It will further be evidenced by reduced requirement for other, symptomatic therapy, i.e. therapy for or intended to restrict or abort symptomatic attack when it occurs, for example anti-inflammatory (e.g. corticosteroid) or bronchodilatory (e.g. $\beta_2$ adrenergic) therapy.

Prophylactic benefit of compounds of formula I, their N-oxides and their salts employed in accordance with the methods of the invention will in particular be apparent in subjects prone to "morning dipping". "Morning dipping" is a recognised asthmatic syndrome, common to a substantial percentage of asthmatics and characterised by an asthma attack, usually in the early hours of the morning, e.g. between the hours of about 4 to 6 am, i.e. at a time normally substantially distant from any previously administered symptomatic asthma therapy, and by which any drug previously taken may be anticipated to have been rendered inactive by metabolic or other procedures of elimination from the body. This nocturnal asthma is harder to control than other forms of asthma and carries with it a higher risk of death. Since compounds of formula I, their N-oxides and their salts exert prophylactic rather than symptomatic effect and by their action on basal pathology (e.g. airways hyperreactivity) exert advance protective action against future attack, appropriate administration on the day preceding will act to abrogate "morning dipping" on the day following.

Accordingly the present invention further provides:

D. A method for reducing requirement for symptomatic drug therapy, e.g. anti-inflammatory or bronchodilator drug therapy, in a subject receiving such therapy, for the treatment, e.g. for the alleviation of symptoms of obstructive or inflammatory airways disease, e.g. asthma, which method comprises administering to said subject a prophylactically effective amount of compounds of formula I, their N-oxides and their salts as well as E. A method for the treatment of "morning dipping" in a subject in need thereof which method comprises administering to said subject a prophylactically effective amount of compounds of formula I, their N-oxides and their salts.

The present invention also provides:

F. Compounds of formula I, their N-oxides and their salts for use in a method of treatment as defined under any one of A to E above;

G. Compounds of formula I, their N-oxides and their salts for use in the preparation of a pharmaceutical composition, for use in a method of treatment as defined under any one of A to E above;

As will be appreciated, in practicing the present invention compounds of formula I, their N-oxides and their salts are administered in advance of asthma attack and appropriately in accordance with a suitable prophylactic regimen, e.g. on a continuing or regular basis, e.g. daily, e.g. a daily dosage rates as hereinafter discussed.

Utility of compounds of formula I, their N-oxides and their salts in accordance with the present invention may be demonstrated, for example, in test models and in clinical trials, e.g. performed as follows:

MODEL A: SUPPRESSION OF AIRWAYS HYPERREACTIVITY—PAF TREATED ANIMALS

Naive (i.e. non-presensitised) guinea-pigs are anaethetised with phenobarbital (100 mg/kg i.p.) and pentobarbital (30 mg/kg i.p.) and paralysed with gallamine (10 mg/kg i.m.). Animals are ventilated via a tracheal cannula (8 ml/kg, 1 Hz). Ventilation is monitored by a Fleisch flow transducor in line with the inspiratory circuit. When making measurements of flow, coincident pressure changes in the thorax are monitored directly via an intrathoracic trochar, permitting display of differential pressure relative to the trachea. From this information, resistance and compliance are calculated at each inspiration. Intravenous injection of low dose bombesin (240 ng/kg) established airways sensitivity to spasmogens. Following infusion of PAF (platelet activating factor) over 1 hour (total dose=600 ng/kg), repeated injection of low dose bombesin or histamine reveals development of airways hyperreactivity, which can conveniently be expressed as the paired difference between the response amplitude before and after PAF exposure.

Administration of compounds of formula I, their N-oxides and their salts (e.g. PCO 400) as a bolus or as a sustained infusion during PAF exposure at dosages of from about 0.06 to about 1 mg/kg diminishes the incremental increase of responses to bombesin/histamine.

CLINICAL TRIALS

1. Utility in obstructive inflammatory airways disease, e.g. asthma

Prophylactic efficacy of compounds of formula I, their N-oxides and their salts (e.g. PCO 400) may be determined in clinical trials of classic design, e.g. involving subjects exhibiting allergic (atopic) bronchoconstrictor response, by administration of test medication or placebo 1 to 2 hours prior to allergen challenge, or by administration of test medication at regular dosage rates (e.g. 2 or 3 times daily) or placebo over a period of 1 to 7 days prior to allergen challenge.

Suitable individual dosages in such clinical trials are as hereinafter indicated, e.g. for compounds of formula I, their N-oxides and their salts, for example PCO 400 comprise e.g. ca. 0.5 to 1.0 mg (for single administration or administration 2 to 3×daily).

Both acute (0 to 1 hour) and long-term (up to 12 hour) change in lung function is determined post-medication by measurement of lung function parameters, e.g. as follows:

a) FVC; FEV 0.5; FEV 1.0; FEV 3.0;
b) FEV 0.5/FVC; FEV 1/FVC; FEV 3/FVC;
c) PEF; FEF 25-75%; FEF 75-85%; FEF 25%; FEF 50%; FEF 75%; FEF 0.2-2.2;
d) Flow expiratory curve and flow inspiratory curve.

Tolerance of medication and possible occurrence of side effects are also reported.

In addition to monitoring of lung function, blood eosinophil levels are also monitored and the incidence of activated eosinophils and eosinophil secretory proteins is determined. In individual studies, subjects are also subjected to lung lavage and the presence of eosinophils and platelets and their respective secretory products determined before and after exposure to allergen.

In clinical trials designed in accordance with the above principles, compounds of formula I, their N-oxides and their salts, for example PCO 400, provide advance protection against bronchoconstrictor response to allergen compared with control subjects receiving placebo only, on administration at dosages indicated. Similar results are obtained with other compounds of formula I, their N-oxides and their salts at the same or equivalent dosage rates.

2. Prophylactic efficacy in asthma

Prophylactic efficacy of compounds of formula I, their N-oxides and their salts may also be demonstrated in clinical trials involving administration to groups of asthmatic subjects on a regular daily basis over periods from at least 2, preferably 3 months, up to 6 months and more. Initial dosaging for a compound of formula I, its N-oxide and salt, for example PCO 400, is of the order of from 0.5 to 1.0 mg administered once or in divided dosages 2 or 3×daily, for oral administration, with subsequent reduction in appropriate cases to a maintenance dosage of 0.25 to 0.5 mg per day orally. During the course of the trial subjects are monitored continually and all relevant parameters recorded, including lung function, alterations in the incidence of activated eosinophils or the release of eosinophil products into the blood or bronchial fluids and/or changes in the function of platelets ex vivo and, in particular, frequency and severity of asthma exacerbation or attack. Additional bronchodilator therapy is provided on the occasion of any such attack.

Subjects receiving therapy comprising a compound of formula I, its N-oxide and its salt, e.g. PCO 400, at dosages indicated above or other compounds of formula I, their N-oxides and their salts at the same or equivalent dosage rates, show marked reduction in frequency of asthma exacerbation or attack, tending with duration of the trial, to lead to freedom from attack as compared with subjects receiving alternative, non-prophylactic therapy. Where participating subjects are initially dependent on concomitant, bronchodilator e.g. methylxanthine or $\beta_2$-agonist therapy, increasingly reduced need for concomitant therapy is also observed.

3. Utility in the treatment of pneumoconiosis

The trial is performed analogously to 2 above but with groups of subjects having a history of pneumoconiosis, e.g. characterised by events of restricted lung function, for example including difficulty in breathing, wheezing, dyspnea or occasional bronchoconstrictor attack and a record of pneumoconiosis-related work absenteeism. Suitable subjects include cotton-mill workers exhibiting severe byssinosis.

Compounds of formula I, their N-oxides and their salts administered daily at dosage rates as set forth in 2 above, over periods in excess of 2, preferably in excess of 3 months. During the course of the trial, subjects are monitored continually and all relevant parameters are recorded, including basal lung-function, frequency of attack with impairment of lung-function, requirement for other medication and frequency of absenteeism attributable to pneumoconiosis.

Subjects receiving therapy in accordance with the invention exhibit overall improvement in basal lung-function during the course of the trial accompanied by reduced frequency of attack and absenteeism as well, in cases where frequent use of alternative medication is recorded at trial entry, reduced need for concomitant medication.

In the above clinical trials, compounds of formula I, their N-oxides and their salts (e.g. PCO 400), are found to be well tolerated both in terms of reported and observed occurrence of side effects.

4. Utility in the treatment of morning dipping

Prophylactic efficacy of compounds of formula I, their N-oxides and their salts may further be demonstrated in clinical trials involving administration to subjects specifically prone to morning dipping. The trial is performed analogously to 2. above.

Compounds of formula I, their N-oxides and their salts administered to groups of subjects daily over periods of, for example, 2 weeks to at least 3 months at dosage rates as set forth in 2. above.

During the course of the trial, subjects are monitored continually and all relevant parameters, in particular lung function parameters such as PEF and FEV1, are recorded.

Subjects receiving therapy in accordance with the invention, e.g. receiving compounds of formula I, their N-oxides and their salts (e.g. PCO 400), exhibit a continuous improvement in lung function parameters with time, in particular shown by a diminished diurnal variation in PEF rates measured morning and evening.

Reduction in asthma symptoms such as wheezing, tightness of the chest, cough etc., and the frequency and severity of asthma attacks is also observed and the exaggerated response to various bronchoconstrictor stimuli, e.g. histamine, methacholine etc., over time is reduced in subjects undergoing treatment.

Dosages of compounds of formula I, their N-oxides and their salts employed in practicing the method of the invention will of course vary depending, e.g. on the particular compound selected, the mode of administration (for example whether oral or by inhalation), the particular condition to be treated, the severity of the condition and the therapy desired.

In general however, compounds of formula I, their N-oxides and their salts will produce satisfactory results in the method of the present invention, as hereinabove described, at dosages substantially equivalent to, or, preferably less than, those dosages employed in indications described for the individual compounds of formula I, their N-oxides and their salts in the art, e.g. in the BASIC TEXTS of e.g. German published application 3815325. Suitable dosages will thus be at the lower end of dosage ranges indicated in the above BASIC TEXTS or down to ca. 5% below these.

With regard to compounds of formula I, their N-oxides and their salts in particular PCO 400, satisfactory results are obtained on oral administration at dosage rates of the order of from about 0.1 to about 2 mg/day, more suitably of from about 0.2 to about 1 mg/day, e.g. of ca 1 mg/day e.g. administered once or in divided dosages 2 to 3×daily or in sustained release form. Suitable unit dosage forms thus contain, e.g. 0.03, 0.1, 0.25, 0.5, 0.75 or 1 mg of active agent per unit dosage.

Where administration by inhalation is practiced dosaging will generally be lower, e.g. of the order of from ca. 50 to 500 µg/day, more suitably of from ca. 50 to 200 µg/day.

For the purposes of prophylactic therapy compounds of formula I, their N-oxides and their salts e.g. PCO 400, will suitably be administered on a regular daily basis over prolonged periods of time, e.g. with multiple administration, for example 2 or 3×daily or with administration in sustained release form. For the prophylactic treatment of "morning dipping" an appropriate daily regimen will suitably incorporate a least one administration, e.g. of the order of from ca. 0.2 mg to 2.0 mg e.g. of ca. 0.5 mg in the evening, suitably shortly prior to sleep.

Pharmaceutical compositions comprising a compound of formula I, its N-oxide and its salts may be prepared in conventional manner, e.g. by admixture with conventional pharmaceutically acceptable diluents and carriers and encapsulation.

Such compositions conveniently contain more than 1% by weight of compounds of formula I, their N-oxides and their salts and may be prepared by conventional techniques to be in conventional forms, for example capsules, tablets, dispersible powders, suspensions, solutions and the like. Suitable pharmaceutical diluents or carriers include, for example, water, alcohols, natural or hardened oils or waxes, calcium and sodium carbonates, calcium phosphate, kaolin, talc and lactose, as well as suitable preserving agents, such as ethyl-p-hydroxybenzoate, suspending agents such as methyl cellulose tragacanth and sodium alginate, wetting agents, such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

Dosages of compounds of formula I, their N-oxides and their salts, e.g. PCO 400, employed in practicing the methods of the present invention, as well as the active ingredient content of dosage forms, in particular unit dosage forms, for use in practicing the methods of the present invention are determined by the particular and novel utility taught. Moreover, specific dosage forms are neither known from nor suggested by the teachings of the art. Such compositions also form an integral part of the present invention.

Accordingly, in a further series of specific embodiments, the present invention also provides:

H. A pharmaceutical composition (e.g. for use in any method as defined under A to E, above) in unit dosage form and comprising a compound of formula I, its N-oxide and its salt, e.g. PCO 400, as active ingredient in an amount of from 0.1 to 2 mg/unit dosage, together with one or more pharmaceutically acceptable diluents or carriers therefor;

I. A pharmaceutical composition according to H for oral administration.

J. A pharmaceutical composition according to H or I comprising a compound of formula I, its N-oxide and its salt, e.g. PCO 400, as active ingredient in an amount of from 0.03 to 1 mg/unit dosage, suitably 0.1, 0.25, 0.5 or 0.75 mg/unit dosage.

K. A pharmaceutical composition in liquid form and suitable or adapted for administration in spray or other liquid particulate form to the internal surfaces of the lung and comprising a compound of formula I, its N-oxides and its salt, e.g. PCO 400, as active ingredient, together with one or more pharmaceutically acceptable liquid diluents or carriers therefor.

L. A process for the preparation of a pharmaceutical composition as defined in any one of H to K above which process comprises intimately admixing a compound of formula I, its N-oxides and its salt, e.g. PCO 400, together with one or more pharmaceutically acceptable diluents or carriers therefor.

Compositions as defined under K above may be prepared in essentially conventional manner. Such compositions include, e.g. solutions or fine dispersions of a compound of formula I, its N-oxid and its salt, e.g. PCO 400, in particular aqueous solutions or dispersions. Such solutions or dispersions will also suitably comprise one or more surfactive agents, e.g. to promote or assist nebulisation or distribution upon adsorption at the lung surface following inhalation. Such compositions will suitably be contained in an appropriate delivery device, e.g. aerosol, nebuliser or atomiser. Such device will preferably be adapted to administer a fixed spray volume on single or multiple, e.g. double or triple, activation, the total amount of compounds of formula I, their N-oxides and their salts delivered in said fixed spray volume being as hereinbefore indicated.

Such device will also suitably be provided with means to facilitate administration of contained composition by inhalation, e.g. as known in the art for other medication applied by inhalation to the internal surfaces of the lungs. Such means may, for example, include provision of an outlet (e.g. nozzle) to said container, shaped or adapted for application of composition exiting through said outlet on actuation of the device.

Compounds of formula I, their N-oxides and their salts are well tolerated at dosages required for use in accordance with the present invention. Thus, the compounds, for example PCO 400, are observed to have minimal central side effects and are substantially non-toxic at dosages up to 318 mg/kg/day in the rat and in dogs have been shown to be well tolerated up to a dosage level of 1 mg/kg/day.

What we claim is:

1. A benzo[b]pyrane or pyranopyridine of formula

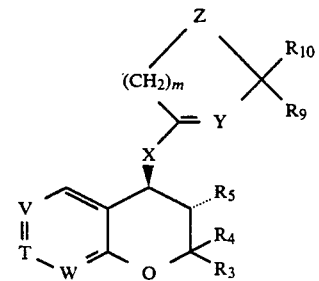

wherein either

A) V denotes $R_1$—C, T denotes $R_2$—C and W denotes H—C, wherein $R_1$ signifies hydrogen, halogen, ethynyl, hydroxy, cyano or the groups of formulae —$NR_6R_8$, —$CO_2R_6$ or —$CONR_6R_7$ and $R_2$ signifies hydrogen, halogen, ($C_{1-4}$)alkoxy, hydroxy or the group of formula —$NR_6R_8$— whereby $R_6$ and $R_7$ independently of one another denote hydrogen or a ($C_{1-4}$)alkyl group and $R_8$ signifies hydrogen, a ($C_{1-4}$)alkyl group, a formyl, an acetyl or a trifluoroacetyl group—or one of $R_1$ and $R_2$ signifies nitro and the other of $R_1$ and $R_2$ is defined as above, or B) V denotes N or the corresponding N-Oxide, T denotes $R_2$—C wherein $R_2$ has the significance given above and W denotes HC, or C) V denotes $R'_1$—C, T denotes H—C and W denotes N, wherein $R_1'$ signifies hydrogen, a cyano or nitro group or D) V denotes N, T denotes H—C and W denotes N, $R_3$ and $R_4$ independently of one another, denote hydrogen or a ($C_{1-4}$)alkyl group or $R_3$ and $R_4$ together signify a group —($CH_2$)n—, whereby n is 2, 3, 4 or 5, $R_5$ signifies hydrogen or $OR_8$, wherein $R_8$ is defined as above, $R_9$ and $R_{10}$ respectively denote hydrogen or methyl or together signify an oxo- or a thio-group, m is 1,2 or 3, X signifies O or $NR_{11}$, whereby $R_{11}$ signifies hydrogen, a ($C_{1-4}$)alkyl-, formyl-, acetyl- or hydroxymethyl group, Y=CH, C-halogen, N, C-formyl or C-hydroxymethyl and Z=$CH_2$, O, S, CH-halogen or $NR_6$, wherein $R_6$ is defined as above and their N-Oxides, their pharmacologically acceptable acid addition salts and quaternary ammonium salts.

2. A benzo[b]pyrane or pyranopyridine according to claim 1 of formula

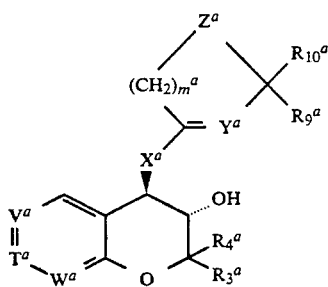

wherein either

A$^a$) V$^a$ denotes R$_1^a$—C, T$^a$ denotes R$_2^a$—C and W$^a$ denotes H—C, wherein R$_1^a$ signifies hydrogen, cyano, halogen, —NR$_6$R$_8$ ethynyl or a group —CO$_2$R$_6$ or —CONR$_6$R$_7$ and R$_2^a$ signifies hydrogen, methoxy, hydroxy or a group of formula —NR$_6$R$_8$, wherein R$_6$, R$_7$ and R$_8$ have the significance given in claim 1, or one of R$_1^a$ and R$_2^b$ denotes nitro and the other of R$_1^a$ and R$_2^b$ is defined as above, or B$^a$) V$^a$ denotes N or the corresponding N-Oxide, T$^a$ denotes R$_2^a$—C wherein R$_2^a$ has the significance given above and W$^a$ denotes H—C, or C$^a$) V$^a$ denotes R$_1^{a'}$—C, T$^a$ denotes H—C and W$^a$ denotes N, wherein R$_1^a$ signifies hydrogen, cyano or nitro or D$^a$) V$^a$ denotes N, T$^a$ denotes H—C and W$^a$ denotes N R$_3^a$ and R$_4^a$ respectively signify hydrogen or (C$_{1-4}$)alkyl or R$_3^a$ and R$_4^a$ together form a group of formula —(CH$_2$)$_{n^a}$—, wherein n$^a$ signifies 2,3 or 4

R$_9^a$ and R$_{10}^a$ respectively signify hydrogen or methyl or together signify an oxo group, m$^a$ = 1 or 2

X$^a$ denotes O or NR$_{11}$, wherein R$_{11}$ possesses the definition given in claim 1, Y$^a$ denotes CH, C-halogen, C-hydroxymethyl, C-formyl or N and Z$^a$ denotes O, NR$_6$, wherein R$_6$ possesses the definition given in claim 1, CH$_2$, CH-halogen or —S— and their N-oxides, their pharmacologically acceptable acid addition salts and quaternary ammonium salts.

3. A benzo[b]pyrane or pyranopyridine according to claim 1 of formula

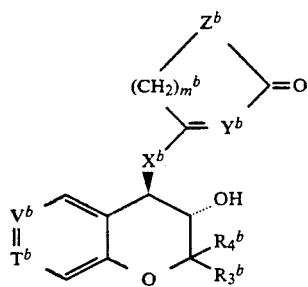

A$^b$) V$^b$ denotes R$_1^b$—C, T$^b$ denotes R$_2^b$—C, wherein R$_1^b$ signifies hydrogen, ethynyl, cyano or a group of formula —NR$_6$R$_8$, —CO$_2$R$_6$ or —CONR$_6$R$_7$ and R$_2^b$ signifies hydrogen, hydroxy or a group of formula —NR$_6$R$_8$ wherein R$_6$, R$_7$ and R$_8$ have the significances given in claim 1, or one of R$_1^b$ and R$_2^b$ signifies nitro and the other of R$_1^b$ and R$_2^b$ is defined as above, or B$^b$) V$^b$ denotes N or the corresponding N-Oxide, T$^b$ denotes R$_2^b$—C, wherein R$_2^b$ has the significance given above, R$_3^b$ and R$_4^b$ respectively signify hydrogen or (C$_{1-4}$)alkyl, or R$_3^b$ and R$_4^b$ together signify a group of formula —(CH$_2$)$_{n^b}$—, wherein n signifies 2,3 or 4, m$^b$ denotes 1, or 2, and X$^b$ denotes O or NR$_{11}$, whereby R$_{11}$ possesses the definition given in claim 1, Y$^b$ denotes CH, C-halogen, C-hydroxymethyl, C-formyl or N and Z$^b$ denotes CH$_2$, CH-halogen, O, S or NR$_6$, wherein R$_6$ possesses the definition given in claim 1, and their N-oxides, their pharmacologically acceptable acid addition salts and quaternary ammonium salts.

4. A compound according to claim 1 selected from:

trans-3,4-dihydro-3-hydroxy-2,2-dimethyl-4-(3-oxo-1-cyclopent-1-enyloxy)-2H-1-benzopyran-6-carbonitrile trans-3,4-dihydro-3-hydroxy-2,2-dimethyl-4-(3-oxo-1-cyclohex-1-enyloxy)-2H-1-benzopyran-6-carbonitrile trans-3,4-dihydro-3-hydroxy-2,2-dimethyl-4-(4-iodo-3-oxo-1-cyclopent-1-enyloxy)-2H-1-benzopyran-6-carbonitrile trans-3,4-dihydro-3-hydroxy-2,2-dimethyl-4-(3-oxo-1-cyclopent-1-enylamino)-2H-1-benzopyran-6-carbonitrile (+)-(3R,4S)-trans-3,4-dihydro-3-hydroxy-2,2-dimethyl-4-(3-oxo-1-cyclopent-1-enyloxy)-2H-1-benzopyran-6-carbonitrile (−)-(3S,4R)-3,4-dihydro-3-hydroxy-2,2-dimethyl-4-(3-oxo-1-cyclopent-1-enyloxy)-2H-1-benzopyran-6-carbonitrile trans-3,4-dihydro-3-hydroxy-2,2-dimethyl-4-[2-oxofuran-4(5H)-ylamino]-2H-benzopyran-6-carbonitrile trans-3,4-dihydro-3-hydroxy-2,2-dimethyl-4-[2-oxofuran-4(5H)-yloxy]-2H-1-benzopyran-6-carbonitrile trans-3,4-dihydro-3-hydroxy-2,2-dimethyl-4-[N-methyl-N-(3-oxo-cyclopent-1-enyl)amino-2H-1-benzopyran-6-carbonitrile trans-3,4-dihydro-3-hydroxy-2,2-dimethyl-4-[N-methyl-N-(2-oxo-furan-4(5H)-yl)amino]-2H-1-benzopyran-6-carbonitrile trans-3,4-dihydro-3-hydroxy-2,2-dimethyl-4-[N-methyl-N-(N-methyl-2-oxo-pyrrzol-4(5H)-yl)amino-]2H-1-benzopyran-6-carbonitrile trans-3,4-dihydro-3-hydroxy-2,2-dimethyl-[2-oxothiophen-4(5H)-yloxy]-2H-1-benzopyran-6-carbonitrile trans-4-[N-formyl-[N-(3-oxo-cyclopent-1-enyl)amino]-3,4-dihydro-3-hydroxy-2,2-dimethyl-2H-1-benzopyran-6-carbonitrile trans-3,4-dihydro-3-hydroxy-4-[N-(2-hydroxymethyl-3-oxo-cyclopent-1-enyl)amino]-2,2-dimethyl-2H-1-benzopyran-6-carbonitrile trans-3,4-dihydro-4-(2-formyl-3-oxo-cyclopent-1-enylamino)-3-hydroxy-2,2-dimethyl-2H-1-benzopyran-6-carbonitrile trans-4-[N-(2-fluoro-3-oxo-cyclopent-1-enyl)-amino]-3,4-dihydro-3-hydroxy-2,2-dimethyl-2H-1-benzopyran-6-carbonitrile trans-4-[N-(2-chloro-3-oxo-cyclopent-1-enyl)-amino]-3,4-dihydro-3-hydroxy-2,2-dimethyl-2H-1-benzopyran-6-carbonitrile trans-4-[N-(2-bromo-3-oxo-cyclopent-1-enyl)-amino-]3,4-dihydro-3-hydroxy-2,2-dimethyl-2H-1-benzopyran-6-carbonitrile 3-amino-[N-(trans-3,4-dihydro-2,2-dimethyl-3-hydroxy-6-nitro-2H(1)-benzopyran-4-yl)]-cyclopent-2-en-1-one trans-3,4-dihydro-3-hydroxy-2,2-dimethyl-4-[N-methyl-N-(2-oxo-furan-4(5H)-yl)-amino]-2H-1-benzopyran-6-carboxylic acid-methylester trans-3,4-dihydro-3-hydroxy-2,2-dimethyl-4-[N-methyl-N-(2-oxo-furan-4(5H)-yl)-amino]-2H-1-benzopyran-6-carboxylic acid-dimethylamide trans-2,2-diethyl-3,4-dihydro-3-hydroxy-4-(3-oxo-cyclopent-1-enyloxy)-2H-1-benzopyran-6-carbonitrile trans-3,4-dihydro-3-hydroxy-4-(3-oxo-cyclopent-1-enyloxy)-spiro[2H-1-benzopyran-2,1'-cyclohexan]-6-carbonitrile trans-3,4-dihydro-2,2-dimethyl-4-(3-oxo-cyclopent-1-enyloxy)-2H-1-benzopyran-6-carbonitrile 3-amino-N-(trans-3,4-dihydro-3-hydroxy-2,2-dimethyl-2H-pyrano[3,2-c]pyridin-4-yl)cyclopent-2-en-1-one 3-amino-N-(trans-3,4-dihydro-3-hydroxy-2,2-dimethyl-2H-pyrano[3,2-c]pyridin-4-yl)cyclopent-2-en-1-on-N-oxide trans-N-acetyl-2,2-diethyl-7-amino-3,4-dihydro-3-hydroxy-4-(3-oxo-cyclopent-1-enyloxy)-2H-1-benzopyran-6-carbonitrile 3-(trans-N-acetyl-6-amino-3,4-dihydro-3-hydroxy-7-nitro-2,2-dimethyl-2H-1-benzopyran-4-oxy)-cyclopent-2-en-1-on 5. The compound according to claim 1, which is (−)-(3S,4R)-3,4-dihydro-3-hydroxy-2,2-dimethyl-4-(3-oxo-1-cyclopent-1-enyloxy)-2H-1-benzopyran-6-carbonitrile.

6. A pharmaceutical composition useful in the treatment of raised blood pressure, vascular disorders, disorders in which a reduction in the tension of the smooth muscles is therapeutically useful, asthma, and obstructive disorders of the respiratory system comprising a therapeutically effective amount of a compound of claim 1 and a pharmaceutically acceptable carrier therefor.

7. A method of preventing or treating raised blood pressure, vascular disorders, and disorders in which a reduction in the tension of the smooth muscles is therapeutically useful which comprises administering to a subject in need of said treatment a therapeutically effective amount of a compound of claim 1.

8. A method of preventing or treating of asthma and obstructive disorders of the respiratory system which comprises administering to a subject in need of said treatment a therapeutically effective amount of a compound of claim 1.

9. A method for the prophylactic treatment of obstructive or inflammatory airways disease in a subject in need thereof, which comprises administering to said subject a prophylactically effective amount of a compound selected from the group consisting of: compounds of formula I according to claim 1 their N-oxides as well as the pharmaceutically acceptable acid addition and quaternary ammonium salts thereof.

10. A method according to claim 8 wherein the compound administered is (−)-(3S,4R)-3,4-dihydro-3-hydroxy-2,2-dimethyl-4-(3-oxo-1-cyclopent-1-enylox-2H-1-benzopyran-6-carbonitrile.

11. A method according to any one of claims 9 or 10 for the inhibition of acute response in hypersensitive subjects following allergen or other challenge eliciting hypersensitivity reaction.

12. A method according to any one of claims 9 or 10 for the suppression of development of airways hyperreactivity subsequent to allergen or other challenge eliciting hypersensitivity reaction.

13. A method according to any one of claims 9 or 10 for the reversal of recently established exacerbation of airways hyperreactivity.

14. A method according to any one of claims 9 or 10 for diminishing basal airways hyperreactivity.

15. A method for the treatment of morning dipping in a subject in need thereof which comprises administering to said subject a prophylactically effective amount of a compound as defined in claims 9 or 10.

16. A pharmaceutical composition: in unit dosage form and comprising a compound of formula I, its N-oxide and its salt according to claim 1, as active ingredient in an amount of from 0.1 to 2 mg/unit dosage, together with one or more pharmaceutically acceptable diluents or carriers therefor; or in liquid form and suitable or adapted for administration in spray or other liquid particulate form and comprising a compound of formula I, its N-oxide and its salt according to claim 1, as active ingredient, together with one or more pharmaceutically acceptable diluents or carriers therefor.

17. A composition according to claim 16 comprising (−)-(3S,4R)-3,4-dihydro-3-hydroxy-2,2-dimethyl-4-(3-oxo-1-cyclopent-1-enyloxy)-2H-1-benzopyran-6-carbonitrile as active ingredient.

18. A composition according to claim 16 or 17 in oral unit dosage form.

19. A composition according to claim 18 comprising (−)-(3S,4R)-3,4-dihydro-3-hydroxy-2,2-dimethyl-4-(2-oxo-1-cyclopent-1-enyloxy)-2H-1-benzopyran-6-carbonitrile as active ingredient in an amount of from 0.1 to 1 mg/unit dosage.

20. A method of preventing or treating asthma and obstructive disorders of the respiratory system which comprises administering to a subject in need of said treatment a therapeutically effective amount of (−)-(3S,4R)-3,4-dihydro-3-hydroxy-2,2-dimethyl-4-(3-oxo-1-cyclopent-1-enyloxy)-2H-1-benzopyran-6-carbonitrile.

21. A method of preventing or treating hypertension and claudication intermittens which comprises administering to a subject in need of said treatment a therapeutically effective amount of (−)-(3S,4R)-3,4-dihydro-3-hydroxy-2,2-dimethyl-4-(3-oxo-1-cyclopent-1-enyloxy)-2H-1-benzopyran-6-carbonitrile.

* * * * *